United States Patent
Li et al.

(10) Patent No.: US 12,086,982 B2
(45) Date of Patent: Sep. 10, 2024

(54) METHOD FOR CONFIRMING CUP-DISC RATIO BASED ON NEURAL NETWORK, APPARATUS, DEVICE, AND COMPUTER READABLE STORAGE MEDIUM

(71) Applicant: PING AN TECHNOLOGY (SHENZHEN) CO., LTD., Guangdong (CN)

(72) Inventors: Ge Li, Guangdong (CN); Guanju Cheng, Guangdong (CN); Chan Zeng, Guangdong (CN); Peng Gao, Guangdong (CN); Guotong Xie, Guangdong (CN)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 393 days.

(21) Appl. No.: 17/612,566

(22) PCT Filed: Oct. 30, 2020

(86) PCT No.: PCT/CN2020/125009
§ 371 (c)(1),
(2) Date: Nov. 18, 2021

(87) PCT Pub. No.: WO2021/189849
PCT Pub. Date: Sep. 30, 2021

(65) Prior Publication Data
US 2022/0309654 A1   Sep. 29, 2022

(30) Foreign Application Priority Data
Sep. 21, 2020   (CN) .................. 202010992346.X (51) Int. Cl.
*G06T 7/00* (2017.01)
*G06T 7/11* (2017.01)
(Continued)

(52) U.S. Cl.
CPC .............. *G06T 7/0012* (2013.01); *G06T 7/11* (2017.01); *G06T 7/12* (2017.01); *G06T 7/62* (2017.01);
(Continued)

(58) Field of Classification Search
CPC ........... G06T 7/0012; G06T 7/62; G06T 7/12; G06T 7/11; G06T 2207/20084; G06T 2207/30041
See application file for complete search history.

(56) References Cited

U.S. PATENT DOCUMENTS

| | | | |
|---|---|---|---|
| 9,684,959 B2 * | 6/2017 | Cheng ................. | G06V 40/197 |
| 11,620,763 B2 * | 4/2023 | Dai ........................... | G06T 7/75 |
| | | | 382/128 |
| 2011/0003880 A1 * | 1/2011 | Bhattacharya .......... | A61P 27/06 |
| | | | 800/9 |

(Continued)

FOREIGN PATENT DOCUMENTS

| | | |
|---|---|---|
| CN | 102112044 A | 6/2011 |
| CN | 109829877 A | 5/2019 |

OTHER PUBLICATIONS

International search report of PCT Patent Application No. PCT/CN2020/125009 issued on Jun. 18, 2021.

*Primary Examiner* — Kevin Ky (57) ABSTRACT

The present disclosure relates to an artificial intelligence field using a neural network, and publishes a method for confirming a cup-disc ratio based on a neural network, an apparatus, a computer device, and a computer readable storage medium. The method includes: obtaining a retinal image, and detecting an optical disc region in the retinal image to obtain the optical disc region; inputting the optical disc region into a pre-trained neural network to obtain a prediction cup-disc ratio and segment images of an optical cup and an optical disc; computing a cup-disc ratio based on the segment images of the optical cup and the optical disc;

(Continued)

and confirming a practical cup-disc ratio based on the prediction cup-disc ratio and the computed cup-disc ratio.

16 Claims, 8 Drawing Sheets

(51) Int. Cl.
  *G06T 7/12* (2017.01)
  *G06T 7/62* (2017.01)
(52) U.S. Cl.
  CPC ............. *G06T 2207/20084* (2013.01); *G06T 2207/30041* (2013.01)

(56) References Cited

U.S. PATENT DOCUMENTS

| | | | | |
|---|---|---|---|---|
| 2012/0230564 | A1* | 9/2012 | Liu | A61B 3/0025 382/128 |
| 2015/0124216 | A1* | 5/2015 | Abramoff | A61B 3/0025 351/246 |
| 2018/0140180 | A1* | 5/2018 | Coleman | G06T 7/0012 |
| 2020/0288972 | A1* | 9/2020 | Park | A61B 3/14 |
| 2020/0401841 | A1* | 12/2020 | Lee | G06V 10/764 |
| 2022/0164947 | A1* | 5/2022 | Yu | G06N 3/08 |
| 2022/0165418 | A1* | 5/2022 | Li | G06V 10/7747 |
| 2022/0189012 | A1* | 6/2022 | Park | G16H 50/20 |
| 2022/0198831 | A1* | 6/2022 | Coleman | G06V 40/19 |
| 2022/0309654 | A1* | 9/2022 | Li | G06T 7/11 |
| 2023/0141896 | A1* | 5/2023 | Liu | A61B 3/0025 351/246 |
| 2023/0337912 | A1* | 10/2023 | Stuchi | A61B 3/1208 |

\* cited by examiner

METHOD FOR CONFIRMING CUP-DISC RATIO BASED ON NEURAL NETWORK, APPARATUS, DEVICE, AND COMPUTER READABLE STORAGE MEDIUM

CROSS-REFERENCE TO RELATED APPLICATION

The present application claims priority to Chinese Patent Application No. 202010992346.X entitled "METHOD FOR CONFIRMING CUP-DISC RATIO BASED ON NEURAL NETWORK, APPARATUS, DEVICE, AND COMPUTER READABLE STORAGE MEDIUM" filed on Sep. 21, 2020, the contents of which is expressly incorporated by reference herein in its entirety.

TECHNICAL FIELD

The present disclosure relates an image processing field, particular to a method for confirming cup-disc ratio based on a neural network, an apparatus, a device, and a computer readable storage medium.

BACKGROUND

Glaucoma is one of three eye diseases, which can cause a loss of sight. Glaucoma is irreversible. Early diagnosis and treatment are important for improving a quality of life. When automatically screening glaucoma, a cup-disc ratio is served as an evaluation index. A retinal image is divided into an optical cup and an optical disc by a dividing method, and the cup-disc ratio is computed based on the optical cup and the optical disc. The dividing method in a related art is affected by a quality of the retinal image, such as an illumination, a shield, and so on, which reduce a dividing accuracy. The computed cup-disc ratio is in a lower accuracy, and missing screening or repetition screening may be generated. Thus, it is necessary to provide a method for improving the accuracy of the cup-disc ratio and reducing the missing screening or repetition screening while automatically screening the glaucoma diseases.

Thus, it is a problem how to improve the accuracy of the cup-disc ratio for improving the accuracy of the cup-disc ratio and reducing the missing screening or repetition screening while automatically screening the glaucoma diseases.

SUMMARY OF THE INVENTION

A method for conforming a cup-disc ratio based on a neural network, the method includes:

Obtaining a retinal image, and detecting an optical disc region in the retinal image to obtain the optical disc region; inputting the optical disc region into a pre-trained neural network to obtain a prediction cup-disc ratio and segment images of an optical cup and an optical disc; computing a cup-disc ratio based on the segment images of the optical cup and the optical disc; and confirming a practical cup-disc ratio based on the prediction cup-disc ratio and the computed cup-disc ratio.

An apparatus for conforming a cup-disc ratio based on a neural network, the method includes:

An image detection module, configured to obtain a retinal image, detect an optical disc region in the retinal image to obtain the optical disc region; a network prediction module, configured to input the optical disc region into a pre-trained neural network to obtain a prediction cup-disc ratio and segment images of an optical cup and an optical disc; a computing confirmation module, configured to compute a cup-disc ratio based on the segment images of the optical cup and the optical disc; and a practical confirmation module, configured to confirm a practical cup-disc ratio based on the prediction cup-disc ratio and the computed cup-disc ratio.

A computer device, the computer device includes a storage and a processor; the storage stores computer programs; the processor executes the computer programs to implement the following steps:

Obtaining a retinal image, and detecting an optical disc region in the retinal image to obtain the optical disc region; inputting the optical disc region into a pre-trained neural network to obtain a prediction cup-disc ratio and segment images of an optical cup and an optical disc; computing a cup-disc ratio based on the segment images of the optical cup and the optical disc; confirming a practical cup-disc ratio based on the prediction cup-disc ratio and the computed cup-disc ratio.

A computer readable storage medium, the computer readable storage medium stores computer programs. The computer programs are executed by a processor for implementing the following steps:

Obtaining a retinal image, and detecting an optical disc region in the retinal image to obtain the optical disc region; inputting the optical disc region into a pre-trained neural network to obtain a prediction cup-disc ratio and segment images of an optical cup and an optical disc; computing a cup-disc ratio based on the segment images of the optical cup and the optical disc; confirming a practical cup-disc ratio based on the prediction cup-disc ratio and the computed cup-disc ratio.

BRIEF DESCRIPTION OF THE FIGURES

Implementations of the present disclosure will now be described, by way of example only, with reference to the attached figures, wherein.

DETAILED DESCRIPTION

In order to making the technical solutions of the present disclose to be more clearer and more understand, the present disclosure is described in detail with reference to the accompanying drawings and the embodiments. Distinctly, the specific embodiments described herein are a part of embodiments of the present disclosure, but not the entire embodiments of the present disclosure. Other embodiment achieved according to the specific embodiments described herein by those of an ordinary skill in the art are within the protecting range of the present disclosure.

The flowchart in drawings is merely an example, the content and operations or steps are not necessary, nor being implemented as the described sequence. For example, some operations/steps can be decomposed, combined, or partially combined, and the execution sequence can be change due to action conditions.

It should be understood that, terms used in the description of the present disclosure are used for the purpose of describing specific embodiments only and are not intended to limit the present disclosure. Terms "a", "an", and "the" in singular forms as used in the description of the present disclosure and in the appended claims are also intended to cover plural forms, unless specified clearly otherwise in the context.

It should be further understood that, the term "and/or" used in the description of the present disclosure and the appended claims means any combination and all possible combinations of one or more the associated listed items, and comprises these combinations.

The present disclosure provides a method for confirming a cup-disc ratio based on a neural network, an apparatus, a computer device, and a computer readable storage medium. The method for confirming the cup-disc ratio based on the neural network is used for screening glaucoma by artificial intelligence, for reducing missing screening or repetition screening.

Hereinafter, some embodiment of the present disclose are further described in detail with reference to the accompanying drawings and the embodiments. The embodiments and features in the embodiments can be combined with each other without conflict.

Figure 1:
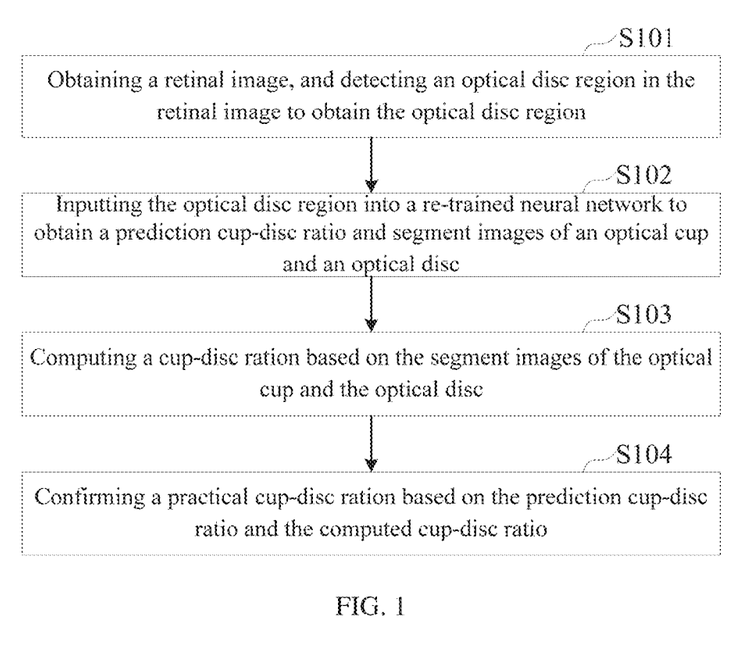
FIG. 1 is a flowchart of an embodiment of a method for confirming a cup-disc ratio based on a neural network.

Referring to FIG. 1, FIG. 1 is a flowchart of a method for confirming the cup-disc ratio based on the neural network. The method for confirming the cup-disc ratio based on the neural network outputs a prediction cup-disc ratio and segments of an optical cup and an optical disc by a pre-trained neural network, computes a cup-disc ratio based on the segments of the optical cup and the optical disc, and confirms a practical cup-disc ratio based on the prediction cup-disc ratio and the computed cup-disc ratio. An accuracy of the cup-disc ratio is improved.

As shown in FIG. 1, the method for confirming the cup-disc ratio based on the neural network includes steps S101 to S104.

In block S101, obtaining a retinal image, and detecting an optical disc region in the retinal image to obtain the optical disc region.

A machine is used for capturing the retinal image and detecting the optical disc region in the retinal image.

Figure 2:
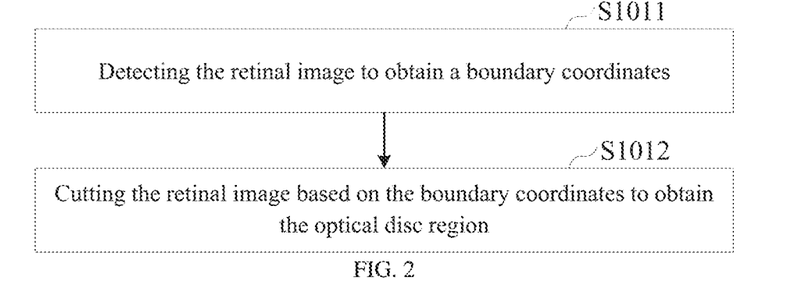
FIG. 2 is a detail flowchart of an embodiment of the step of detecting an optical disc region in the retinal image to obtain the optical disc region.

In some embodiment, as shown in FIG. 2, the step of obtaining a retinal image, and detecting an optical disc region in the retinal image to obtain the optical disc region further includes sub-steps S1011 and S1012.

In block S1011, detecting the retinal image to obtain a boundary coordinate.

Figure 3:
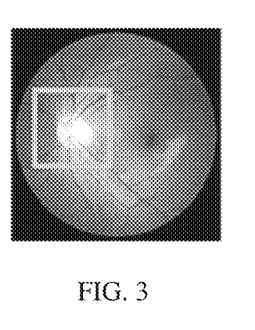
FIG. 3 is a diagram view of an embodiment of the optical disc region in the retinal image.

When detecting the retinal image, there are several target detection technologies can be sued, such as a MaskRCNN model for detecting the retinal image to obtain the boundary coordinates. The boundary coordinates can be coordinates of opposite angle in the optical disc region. FIG. 3 shows the optical disc region. A rectangle frame is the optical disc region obtained by detecting the retinal image, and the boundary coordinates are coordinates of a top left corner and a bottom right corner of the rectangle frame.

In block S1012, cutting the retinal image based on the boundary coordinates to obtain the optical disc region.

Figure 4:
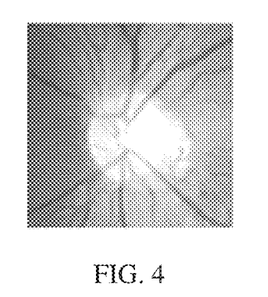
FIG. 4 is a diagram view of the optical disc region.

While cutting the retinal image based on the boundary coordinates based on the boundary coordinates to obtain the optical region, the coordinates of the top left corner and the bottom right corner of the rectangle frame are used for cutting the retinal image to obtain the optical disc region as shown in FIG. 4.

In block S102, inputting the optical disc region into a pre-trained neural network to obtain a prediction cup-disc ratio and segment images of an optical cup and an optical disc.

The optical disc region is inputted into the pre-trained neural network. The neural network forecasts the inputted optical disc region to output the prediction cup-disc ratio and segment images of the optical cup and the optical disc.

In some embodiments, before inputting the optical disc region into the pre-trained neural network, the method further includes: pre-possessing the optical disc region. The pre-processing operation includes a scalable pre-process.

The scalable pre-process converts the image of the optical disc region into a specified size, such as a size in 256*256, which is convenient for the neural network to extract feature from the image of the optical disc region.

Figure 5:
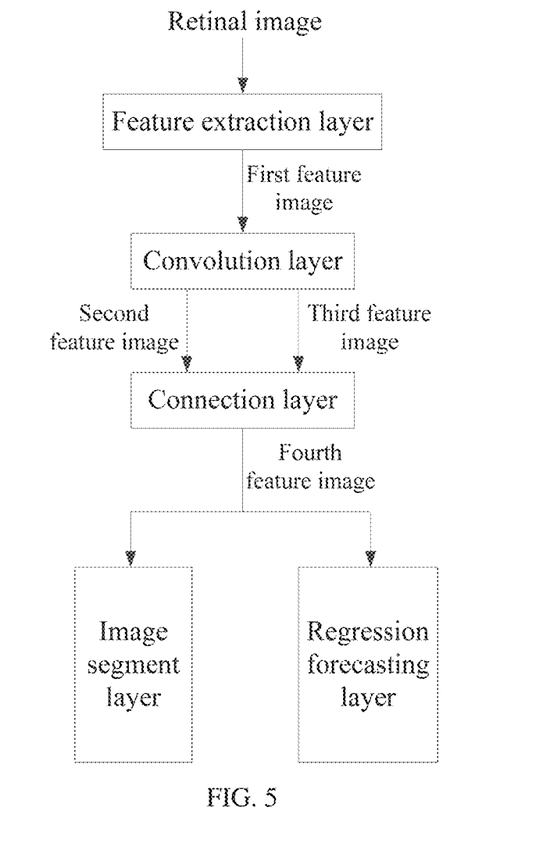
FIG. 5 is a diagram view of a pre-trained neural network.

In some embodiments, the pre-trained neural network includes a feature extraction layer, a convolution layer, a connection layer, a image segment layer, and a regression forecasting layer. FIG. 5 shows a network structure of the pre-trained neural network in one embodiment.

The step of inputting the optical disc region into a pre-trained neural network to obtain a prediction cup-disc ratio and segment images of an optical cup and an optical disc includes: extracting a feature of the optical disc region by the feature extraction layer to obtain a first feature image; executing an convolution of the first feature image by the convolution layer to obtain a second feature image representing a segment image of the cup-disc ratio and a third feature image representing a segment image of the optical disc; connecting the second feature image and the third feature image by the connection layer to obtain a fourth feature image; inputting the fourth feature image into the regression forecasting layer to obtain the prediction cup-disc ratio and the segments images of the optical cup and the optical disc.

While inputting the optical disc region into the neural network, the feature extraction layer in the neural network extracts the feature of the optical disc region, for example, the feature extraction layer uses a mobilenetv2 network to extract the feature of the optical disc region, and the first feature image of the optical disc region is obtained.

When obtaining the first feature image, the convolution layer executes a convolution operation and a dilated convolution operation, for example, the convolution operation uses a 1*1 convolution operation and the dilated convolution operation uses a specified dilated parameter, such as 6. Thus, the second feature image representing the prediction cup-disc ratio and the third feature image representing the prediction segment images of the optical cup and the optical disc are obtained.

In the connection layer, the second feature image representing the prediction cup-disc ratio and the third feature image representing the prediction segment images of the optical cup and the optical disc are connected to obtain the fourth feature image.

Finally, the fourth feature image is inputted into the regression forecasting layer to obtain the prediction cup-disc ratio, and the fourth feature image is also inputted into the regression forecasting layer to obtain the segment image of the optical cup and the optical disc. A loss function of the regression forecasting layer is a minimum mean square error loss function, and a loss function of the image segment layer is a cross entropy loss function.

In block S103, computing a cup-disc ratio based on the segment image of the optical cup and the optical disc.

Due to the segment images of the optical cup and the optical disc outputted by the pre-trained neural network, the cup-disc ratio is computed based on the segment images of the optical cup and the optical disc.

Figure 6:
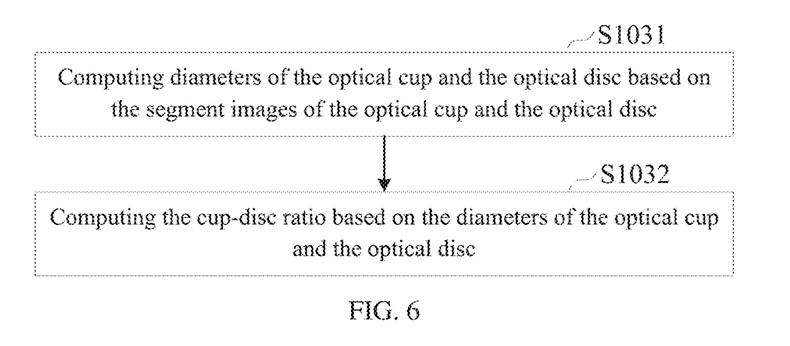
FIG. 6 is a detailed flowchart of the step of computing a cup-disc ratio of FIG. 1.

In some embodiments, referring to FIG. 6, the step of the computing the cup-disc ratio includes: steps S1031 and S1032.

In block S1031, computing diameters of the optical cup and the optical disc based on the segment images of the optical cup and the optical disc, in block S1032, computing the cup-disc ratio based on the diameters of the optical cup and the optical disc.

The diameters of the optical cup and the optical disc are computed based on the segment images of the optical cup and the optical disc, after the diameters of the optical cup and the optical disc are obtained, the cup-disc ratio can be computed according to a formula of a cup-disc ratio. The formula of the cup-disc ratio is CDR=VCD/VDD. CDR represents a computed cup-disc ratio, VCD represents a diameter of the optical cup, and VDD represents a diameter of the optical disc.

In some embodiments, the step of computing the diameters of the optical cup and the optical disc based on the segment images of the optical cup and the optical disc includes: confirming outlines of the optical cup and the optical disc based on the segment images of the optical cup and the optical disc; computing minimum bounding rectangles of the optical cup and the optical disc based on the outlines of the optical cup and the optical disc; computing the diameters of the optical cup and the optical disc based on the minimum bounding rectangles of the optical cup and the optical disc.

By a method for searching a maximum outline, the outlines of the optical cup and the optical disc are extracted from the segment images of the optical cup and the optical disc. The minimum bounding rectangles of the optical cup and the optical disc are obtained based on the outlines of the optical cup and the optical disc using a rotating caliper algorithm. A length of the minimum bounding rectangle of the optical cup along a perpendicular direction is considered as the diameter of the optical cup (VCD). A length of the minimum bounding rectangle of the optical disc along the perpendicular direction is considered as the diameter of the optical disc (VDD).

In block S104, confirming a practical cup-disc ratio based on the prediction cup-disc ratio and the computed cup-disc ratio.

By comparing the prediction cup-disc ratio and the computed cup-disc ratio, the practical cup-disc ratio is confirmed.

In some embodiments, the step of confirming a practical cup-disc ratio based on the computed cup-disc ratio and the prediction cup-disc ratio includes: computing a distance difference between the computed cup-disc ratio and the prediction cup-disc ratio; when the distance difference between the computed cup-disc ratio and the prediction cup-disc ratio is less than or equal to a first threshold value, the computed cup-disc ratio is served as the practical cup-disc ratio; when the distance difference between the computed cup-disc ratio and the prediction cup-disc ratio is larger than a second threshold value, the prediction cup-disc ratio is served as the practical cup-disc ratio; when the distance difference between the computed cup-disc ratio and the prediction cup-disc ratio is larger than the first threshold value and is less than or equal to the second threshold value, an average value of the computed cup-disc ratio and the prediction cup-disc ratio is computed, and the average value is served as the practical cup-disc ratio.

While computing the distance difference between the computed cup-disc ratio and the prediction cup-disc ratio, the distance difference is a value difference between the computed cup-disc ratio and the prediction cup-disc ratio. The practical cup-disc ratio is confirmed in different comparison results by the distance difference between the computed cup-disc ratio and the prediction cup-disc ratio.

When the distance difference between the computed cup-disc ratio and the prediction cup-disc ratio is less than the first threshold value, the computed cup-disc ratio is more accurate than the prediction cup-disc ratio, and the computed cup-disc ratio is served as the practical cup-disc ratio. The first threshold value can be 0.05.

When the distance difference between the computed cup-disc ratio and the prediction cup-disc ratio is larger than the second threshold value, the prediction cup-disc ratio is more accurate than the computed cup-disc ratio, and the prediction cup-disc ratio is served as the practical cup-disc ratio. The second threshold value can be 0.1.

When the distance difference between the computed cup-disc ratio and the prediction cup-disc ratio is larger than the first threshold value, and is less than or equal to the second threshold value, the computed cup-disc ratio and the prediction cup-disc ratio need to be integrated, for example, the average value of the computed cup-disc ratio and the prediction cup-disc ratio is served as the practical cup-disc ratio.

The practical cup-disc ratio can be computed by the formula as below.

$$C = \begin{cases} C1, & \text{if } |C1 - C2| \le 0.05 \\ C2, & \text{if } |C1 - C2| > 0.10 \\ \dfrac{C1 + C2}{2}, & \text{other} \end{cases}$$

C represents the practical cup-disc ratio, C1 represents the computed cup-disc ratio, and the C2 represents the prediction cup-disc ratio.

Based on the method for confirming the cup-disc ratio based on the neural network, the retinal image is obtained and detected to obtain the optical disc region, the optical disc region is inputted into the pre-trained neural network to obtain the prediction cup-disc ratio and segment images of the optical cup and the optical disc. The cup-disc ratio is computed based on the segment images of the optical cup and the optical disc. The practical cup-disc ratio is confirmed based on the computed cup-disc ratio and the prediction cup-disc ratio. While confirming the cup-disc ratio, an dependency on the segment images of the optical cup and the optical disc is reduced, and the accuracy of the cup-disc ratio is improved.

Figure 7:
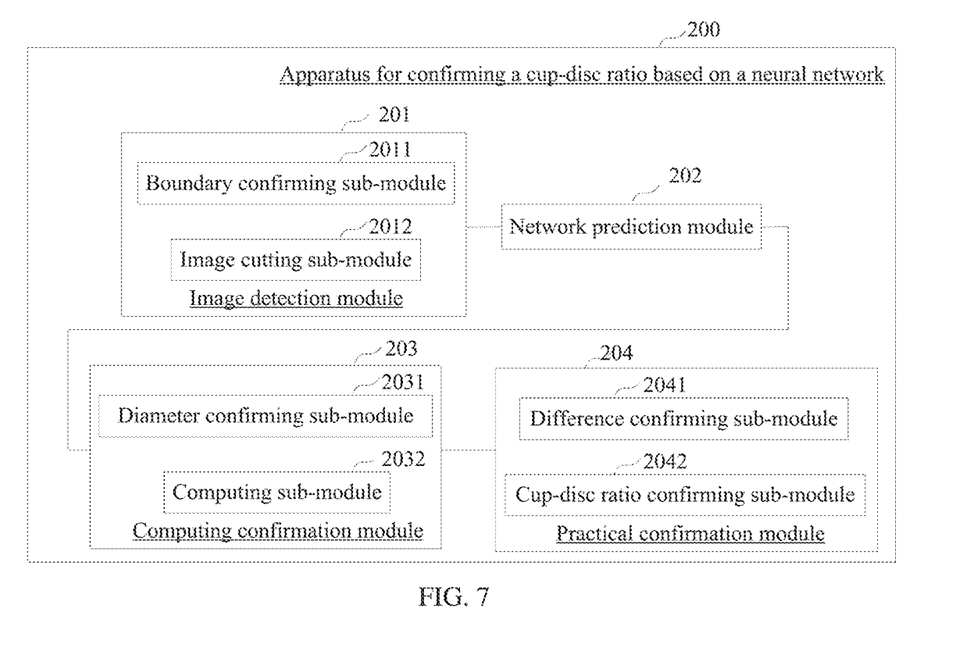
FIG. 7 is a diagram view of an embodiment of an apparatus for confirming a cup-disc ratio based on a neural network.

FIG. 7 shows an embodiment of an apparatus for confirming a cup-disc ratio based on a neural network. The apparatus for confirming the cup-disc ratio based on the neural network implements the method for confirming the cup-disc ratio based on the neural network. The apparatus for confirming the cup-disc ratio based on the neural network is configured in a server or a terminal device.

The server can be an independent server or a server cluster including multiple servers. The terminal device can be an electric device, such as, a mobile phone, a tablet, a notebook, a desktop, a personal digital assistance, or a wearable device.

As shown in FIG. 7, the apparatus 200 for confirming a cup-disc ratio based on a neural network includes: an image detection module 201, a network prediction module 202, a computing confirmation module 203, and a practical confirmation module 204.

The image detection module 201 is configured to obtain a retinal image, detect an optical disc region in the retinal image to obtain the optical disc region.

The image detection module 201 further includes a boundary confirming sub-module 2011 and an image cutting sub-module 2012.

In detail, the boundary confirming sub-module 2011 is configured to detect the retinal image to obtain a boundary coordinate. The image cutting sub-module 2012 is configured to cut the retinal image based on the boundary coordinates to obtain the optical disc region.

The network prediction module 202 is configured to input the optical disc region into a pre-trained neural network to obtain a prediction cup-disc ratio and segment images of an optical cup and an optical disc.

The computing confirmation module 203 is configured to compute a cup-disc ratio based on the segment images of the optical cup and the optical disc.

The computing confirmation module 203 further includes a diameter confirming sub-module 2031 and a computing sub-module 2032.

In detail, the diameter confirming sub-module 2031 is configured to compute diameters of the optical cup and the optical disc based on the segment images of the optical cup and the optical disc, and the computing sub-module 2032 is configured to compute the cup-disc ratio based on the diameters of the optical cup and the optical disc.

The practical confirmation module 204 is configured to confirm a practical cup-disc ratio based on the prediction cup-disc ratio and the computed cup-disc ratio.

It should be understood that, for simplicity and clarification, people having ordinary skill in the art should be able to refer the corresponding operations and the procedures of the method for confirming the cup-disc ratio based on the neural network as described above for the operating procedures of the aforementioned apparatus for confirming the cup-disc ratio based on the neural network and modules, and thus the description will not be repeated.

The apparatus for confirming the cup-disc ratio based on the neural network can be executed in a manner of computer programs. The computer programs can be implemented in a computer device as shown in FIG. 8.

Figure 8:
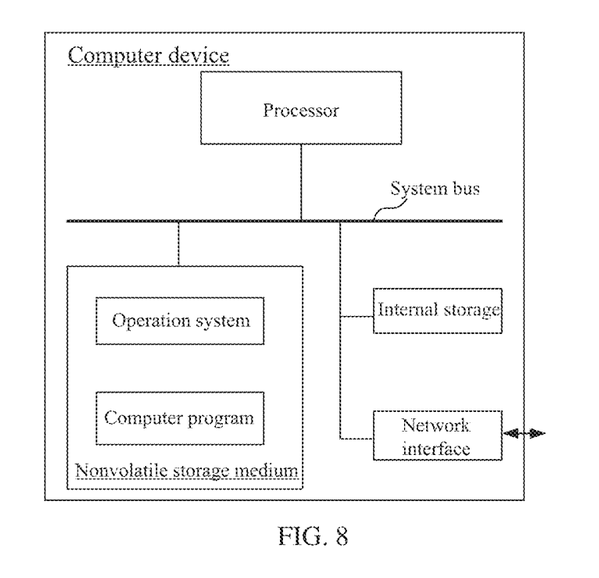
FIG. 8 is a diagram view of an embodiment of a computer device.

Referring to FIG. 8, FIG. 8 shows a computer device. The computer device can be a terminal device or a server.

As shown in FIG. 8, the computer device includes a processor, a storage, and a network interface, which are connected through a system bus. The storage can include a non-volatile storage and an internal storage.

The non-volatile storage can store an operation system and computer programs. The computer programs include program instructions. When the computer instructions being executed, the processor implements a method for confirming the cup-disc ratio based on the neural network.

The processor is configured to provide computation and control ability, for supporting an operation of the computer device.

The internal storage provides an operation environment of the computer instructions of the non-volatile storage. When the computer instructions being executed, the processor implements the method for confirming the cup-disc ratio based on the neural network.

The network interface is configured to provide a network communication, such as sending an assigned task, and so on. It is understood that, the structure as shown in FIG. 8 is a partial structure related to the present disclosure, and are not intended to limit the computer device applied the present disclosure. The computer device can include more or less components, or some components being combined, or different components.

It is understood that, the processor can be a central processing unit (CPU), and can be other general processor, a digital signal processor (DSP), an application specific integrated circuit (ASIC), a field programmable gate array (FPGA), or other programmable logic device, a separate gate or transistor logic device, a separate hardware component, and so on. The general processor can be a microprocessor, other regular data processing chips, and so on.

In one embodiment, the processor executes the computer programs stored in the storage to implement the following steps: obtaining a retinal image, and detecting an optical disc region in the retinal image to obtain the optical disc region; inputting the optical disc region into a pre-trained neural network to obtain a prediction cup-disc ratio and segment images of an optical cup and an optical disc; computing a cup-disc ratio based on the segment images of the optical cup and the optical disc; confirming a practical cup-disc ratio based on the prediction cup-disc ratio and the computed cup-disc ratio.

In one embodiment, when the processor executes the computer programs stored in the storage to implement the step of obtaining a retinal image, and detecting an optical disc region in the retinal image to obtain the optical disc region, the processor further executes the computer programs stored in the storage to implement the following steps: detecting the retinal image to obtain a boundary coordinates; and cutting the retinal image based on the boundary coordinates to obtain the optical disc region.

In one embodiment, before the processor executes the computer programs stored in the storage to implement the step of inputting the optical disc region into the pre-trained neural network to obtain the prediction cup-disc ratio and segment images of the optical cup and the optical disc, the processor further executes the computer programs stored in the storage to implement the following step: pre-possessing the optical disc region. The pre-processing operation includes a scalable pre-process.

In one embodiment, the pre-trained neural network includes a feature extraction layer, a convolution layer, a connection layer, a image segment layer, and a regression forecasting layer. While the processor executes the computer programs stored in the storage to implement the step of inputting the optical disc region into the pre-trained neural network to obtain the prediction cup-disc ratio and segment images of the optical cup and the optical disc, the processor further executes the computer programs stored in the storage to implement the following steps: extracting a feature of the optical disc region by the feature extraction layer to obtain a first feature image; executing an convolution of the first feature image by the convolution layer to obtain a second feature image representing a segment image of the cup-disc ratio and a third feature image representing a segment image of the optical disc; connecting the second feature image and the third feature image by the connection layer to obtain a fourth feature image; inputting the fourth feature image into the regression forecasting layer to obtain the prediction cup-disc ratio and the segments images of the optical cup and the optical disc.

In one embodiment, when the processor executes the computer programs stored in the storage to implement the step of computing the cup-disc ratio based on the segment images of the optical cup and the optical disc, the processor further executes the computer programs stored in the storage to implement the following steps: computing diameters of the optical cup and the optical disc based on the segment images of the optical cup and the optical disc; and computing the cup-disc ratio based on the diameters of the optical cup and the optical disc.

In one embodiment, when the processor executes the computer programs stored in the storage to implement the step of computing diameters of the optical cup and the optical disc based on the segment images of the optical cup and the optical disc, the processor further executes the computer programs stored in the storage to implement the following steps: confirming outlines of the optical cup and the optical disc based on the segment images of the optical cup and the optical disc; computing minimum bounding rectangles of the optical cup and the optical disc based on the outlines of the optical cup and the optical disc; computing the diameters of the optical cup and the optical disc based on the minimum bounding rectangles of the optical cup and the optical disc.

In one embodiment, when the processor executes the computer programs stored in the storage to implement the step of confirming the practical cup-disc ratio based on the prediction cup-disc ratio and the computed cup-disc ratio, the processor further executes the computer programs stored in the storage to implement the following steps: computing a distance difference between the computed cup-disc ratio and the prediction cup-disc ratio; when the distance difference between the computed cup-disc ratio and the prediction cup-disc ratio is less than or equal to a first threshold value, the computed cup-disc ratio is served as the practical cup-disc ratio; when the distance difference between the computed cup-disc ratio and the prediction cup-disc ratio is larger than a second threshold value, the prediction cup-disc ratio is served as the practical cup-disc ratio; when the distance difference between the computed cup-disc ratio and the prediction cup-disc ratio is larger than the first threshold value and is less than or equal to the second threshold value, an average value of the computed cup-disc ratio and the prediction cup-disc ratio is computed, and the average value is served as the practical cup-disc ratio.

The present disclosure also provides a computer readable storage medium. The computer readable storage medium stores computer programs. The computer programs include program instructions. The processor executes the program instructions to implement the following steps:

Obtaining a retinal image, and detecting an optical disc region in the retinal image to obtain the optical disc region; inputting the optical disc region into a pre-trained neural network to obtain a prediction cup-disc ratio and segment images of an optical cup and an optical disc; computing a cup-disc ratio based on the segment images of the optical cup and the optical disc; confirming a practical cup-disc ratio based on the prediction cup-disc ratio and the computed cup-disc ratio.

The computer readable storage medium can be an internal storage of the foregoing computer device, such as a hard disk or a memory. The computer readable storage medium also can be external storage device of the computer device, such as a plug-in hard disk in the computer device, a smart media card (SMC), a secure digital (SD), a flash card, and so on.

In another embodiment, for ensuring a privacy and a security of the data in the method for confirming the cup-disc ratio based on the neural network of the present disclosure, the foregoing data are stored in a node of a blockchain. For example, the retinal image and segment images, which are stored in the node of the blockchain.

It is understood that, the blockchain is a novel application mode based on computer technologies, such as distribution data storage, node-to-node transmission, consensus mechanism, and encryption algorithm.

The foregoing implementations are merely preferably embodiments of the present disclosure, and are not intended to limit the protection scope of the present disclosure. Any equivalent structure variation using the present disclosure and drawings, being directly or indirectly used in other related technical fields shall all fall into the protection scope of the present disclosure. Thus, the protection scope of the present disclosure shall be subjected to the protection scope of the claims.

What is claimed is:

1. A method for confirming a cup-disc ratio based on a neural network; the method comprising following steps:
   obtaining a retinal image, and detecting an optical disc region in the retinal image to obtain the optical disc region;
   inputting the optical disc region into a pre-trained neural network stored in a storage, by a processor, and setting a result outputted by the pre-trained neural network as a prediction cup-disc ratio and segment images of an optical cup and an optical disc;
   computing a cup-disc ratio based on the segment images of the optical cup and the optical disc; and
   confirming a practical cup-disc ratio based on the prediction cup-disc ratio and the computed cup-disc ratio;
   wherein the neural network comprises a feature extraction layer, a convolution layer, a connection layer, an image segment layer, and a regression forecasting layer; the step of inputting the optical disc region into a pre-trained neural network to obtain a prediction cup-disc ratio and segment images of an optical cup and an optical disc further comprising:
   extracting a feature of the optical disc region by the feature extraction layer to obtain a first feature image;
   executing a convolution of the first feature image by the convolution layer to obtain a second feature image representing a segment image of the cup-disc ratio and a third feature image representing a segment image of the optical disc;
   connecting the second feature image and the third feature image by the connection layer to obtain a fourth feature image; and
   inputting the fourth feature image into the regression forecasting layer to obtain the prediction cup-disc ratio and the segments images of the optical cup and the optical disc.

2. The method of claim 1, wherein the step of obtaining a retinal image, and detecting an optical disc region in the retinal image to obtain the optical disc region comprising:
   detecting the retinal image to obtain a boundary coordinate; and
   cutting the retinal image based on the boundary coordinates to obtain the optical disc region.

3. The method of claim 1, wherein before inputting the optical disc region into the pre-trained neural network, the method further comprising:
pre-processing the optical disc region; the pre-processing operation comprises a scalable pre-process.

4. The method of claim 1, wherein the step of computing a cup-disc ratio based on the segment images of the optical cup and the optical disc further comprising:
computing diameters of the optical cup and the optical disc based on the segment images of the optical cup and the optical disc; and
computing the cup-disc ratio based on the diameters of the optical cup and the optical disc.

5. The method of claim 4, wherein the step of computing diameters of the optical cup and the optical disc based on the segment images of the optical cup and the optical disc further comprising:
confirming outlines of the optical cup and the optical disc based on the segment images of the optical cup and the optical disc;
computing minimum bounding rectangles of the optical cup and the optical disc based on the outlines of the optical cup and the optical disc; and
computing the diameters of the optical cup and the optical disc based on the minimum bounding rectangles of the optical cup and the optical disc.

6. The method of claim 1, wherein the step of confirming a practical cup-disc ratio based on the prediction cup-disc ratio and the computed cup-disc ratio further comprising:
computing a distance difference between the computed cup-disc ratio and the prediction cup-disc ratio;
when the distance difference between the computed cup-disc ratio and the prediction cup-disc ratio is less than or equal to a first threshold value, the computed cup-disc ratio serving as the practical cup-disc ratio;
when the distance difference between the computed cup-disc ratio and the prediction cup-disc ratio is larger than a second threshold value, the prediction cup-disc ratio serving as the practical cup-disc ratio; and
when the distance difference between the computed cup-disc ratio and the prediction cup-disc ratio is larger than the first threshold value and is less than or equal to the second threshold value, computing an average value of the computed cup-disc ratio and the prediction cup-disc ratio, and the average value serving as the practical cup-disc ratio.

7. A computer device, the computer device comprises a storage and a processor;
the storage stores computer programs; and
the processor executes the computer programs to implement the following steps:
obtaining a retinal image, and detecting an optical disc region in the retinal image to obtain the optical disc region;
inputting the optical disc region into a pre-trained neural network stored in the storage, by the processor, and setting a result outputted by the pre-trained neural network as a prediction cup-disc ratio and segment images of an optical cup and an optical disc;
computing a cup-disc ratio based on the segment images of the optical cup and the optical disc; and
confirming a practical cup-disc ratio based on the prediction cup-disc ratio and the computed cup-disc ratio;
wherein the neural network comprises a feature extraction layer, a convolution layer, a connection layer, an image segment layer, and a regression forecasting layer; the step of inputting the optical disc region into a pre-trained neural network to obtain a prediction cup-disc ratio and segment images of an optical cup and an optical disc further comprising:
extracting a feature of the optical disc region by the feature extraction layer to obtain a first feature image;
executing a convolution of the first feature image by the convolution layer to obtain a second feature image representing a segment image of the cup-disc ratio and a third feature image representing a segment image of the optical disc;
connecting the second feature image and the third feature image by the connection layer to obtain a fourth feature image; and
inputting the fourth feature image into the regression forecasting layer to obtain the prediction cup-disc ratio and the segments images of the optical cup and the optical disc.

8. The computer device of claim 7, wherein the step of obtaining a retinal image, and detecting an optical disc region in the retinal image to obtain the optical disc region comprising:
detecting the retinal image to obtain a boundary coordinate; and
cutting the retinal image based on the boundary coordinates to obtain the optical disc region.

9. The computer device of claim 7, wherein before inputting the optical disc region into the pre-trained neural network, the method further comprising:
pre-processing the optical disc region; the pre-processing operation comprises a scalable pre-process.

10. The computer device of claim 7, wherein the step of computing a cup-disc ratio based on the segment images of the optical cup and the optical disc further comprising:
computing diameters of the optical cup and the optical disc based on the segment images of the optical cup and the optical disc; and
computing the cup-disc ratio based on the diameters of the optical cup and the optical disc.

11. The computer device of claim 10, wherein the step of computing diameters of the optical cup and the optical disc based on the segment images of the optical cup and the optical disc further comprising:
confirming outlines of the optical cup and the optical disc based on the segment images of the optical cup and the optical disc;
computing minimum bounding rectangles of the optical cup and the optical disc based on the outlines of the optical cup and the optical disc; and
computing the diameters of the optical cup and the optical disc based on the minimum bounding rectangles of the optical cup and the optical disc.

12. The computer device of claim 7, wherein the step of confirming a practical cup-disc ratio based on the prediction cup-disc ratio and the computed cup-disc ratio further comprising:
computing a distance difference between the computed cup-disc ratio and the prediction cup-disc ratio;
when the distance difference between the computed cup-disc ratio and the prediction cup-disc ratio is less than or equal to a first threshold value, the computed cup-disc ratio serving as the practical cup-disc ratio;
when the distance difference between the computed cup-disc ratio and the prediction cup-disc ratio is larger than a second threshold value, the prediction cup-disc ratio serving as the practical cup-disc ratio; and when the distance difference between the computed cup-disc ratio and the prediction cup-disc ratio is larger than the first threshold value and is less than or equal to the second threshold value, computing an average value of the computed cup-disc ratio and the prediction cup-disc ratio, and the average value serving as the practical cup-disc ratio.

13. A non-transitory computer readable storage medium, the computer readable storage medium stores computer programs; the computer programs are executed by at least one processor to implement the following steps:

obtaining a retinal image, and detecting an optical disc region in the retinal image to obtain the optical disc region;

inputting the optical disc region into a pre-trained neural network stored in the computer readable storage medium, by the at least one processor, and setting a result outputted by the pre-trained neural network as a prediction cup-disc ratio and segment images of an optical cup and an optical disc;

computing a cup-disc ratio based on the segment images of the optical cup and the optical disc; and confirming a practical cup-disc ratio based on the prediction cup-disc ratio and the computed cup-disc ratio;

wherein the neural network comprises a feature extraction layer, a convolution layer, a connection layer, an image segment layer, and a regression forecasting layer; the step of inputting the optical disc region into a pre-trained neural network to obtain a prediction cup-disc ratio and segment images of an optical cup and an optical disc further comprising:

extracting a feature of the optical disc region by the feature extraction layer to obtain a first feature image;

executing a convolution of the first feature image by the convolution layer to obtain a second feature image representing a segment image of the cup-disc ratio and a third feature image representing a segment image of the optical disc;

connecting the second feature image and the third feature image by the connection layer to obtain a fourth feature image; and inputting the fourth feature image into the regression forecasting layer to obtain the prediction cup-disc ratio and the segments images of the optical cup and the optical disc.

14. The non-transitory computer readable storage medium of claim 13, wherein the step of obtaining a retinal image, and detecting an optical disc region in the retinal image to obtain the optical disc region comprising:

detecting the retinal image to obtain a boundary coordinate; and cutting the retinal image based on the boundary coordinates to obtain the optical disc region.

15. The non-transitory computer readable storage medium of claim 13, wherein before inputting the optical disc region into the pre-trained neural network, the method further comprising:

pre-processing the optical disc region; the pre-processing operation comprises a scalable pre-process.

16. The non-transitory computer readable storage medium of claim 13, wherein the step of computing a cup-disc ratio based on the segment images of the optical cup and the optical disc further comprising:

computing diameters of the optical cup and the optical disc based on the segment images of the optical cup and the optical disc; and computing the cup-disc ratio based on the diameters of the optical cup and the optical disc.

\* \* \* \* \*